United States Patent
Tran et al.

(10) Patent No.: US 10,064,614 B2
(45) Date of Patent: Sep. 4, 2018

(54) DEPRESSOR/RETRACTOR

(71) Applicant: The Nemours Foundation, Jacksonville, FL (US)

(72) Inventors: Neil Nghia Tran, Ambler, PA (US); Tariq Rahman, Moylan, PA (US); Thomas H. Shaffer, Chadds-Ford, PA (US); Jordan Wang, Chadds-Ford, PA (US); Whitney Sample, Wilmington, DE (US)

(73) Assignee: THE NEMOURS FOUNDATION, Jacksonville, FL (US)

( * ) Notice: Subject to any disclaimer, the term of this patent is extended or adjusted under 35 U.S.C. 154(b) by 226 days.

(21) Appl. No.: 14/661,767

(22) Filed: Mar. 18, 2015

(65) Prior Publication Data
US 2015/0265267 A1   Sep. 24, 2015

Related U.S. Application Data

(60) Provisional application No. 61/954,863, filed on Mar. 18, 2014.

(51) Int. Cl.
| | |
|---|---|
| *A61B 17/02* | (2006.01) |
| *G05B 15/02* | (2006.01) |
| *B33Y 80/00* | (2015.01) |
| *A61B 17/24* | (2006.01) |
| *B29C 64/386* | (2017.01) |
| *B33Y 50/02* | (2015.01) |
| *A61B 17/32* | (2006.01) |
| *A61B 17/34* | (2006.01) |

(52) U.S. Cl.
CPC .......... *A61B 17/0206* (2013.01); *A61B 17/02* (2013.01); *A61B 17/0293* (2013.01); *A61B 17/24* (2013.01); *B29C 64/386* (2017.08); *B33Y 80/00* (2014.12); *G05B 15/02* (2013.01); *A61B 2017/320052* (2013.01); *A61B 2017/345* (2013.01); *B33Y 50/02* (2014.12)

(58) Field of Classification Search
CPC ....... A61B 1/24–1/253; A61B 17/3423; A61B 2017/345; A61B 1/32; A61M 16/049
USPC ......................................................... 600/237
See application file for complete search history.

(56) References Cited

U.S. PATENT DOCUMENTS

| | | | |
|---|---|---|---|
| 2,437,812 A | 11/1944 | Freel | |
| 3,863,627 A | 2/1975 | Bouffard | |
| 8,740,788 B1 | 6/2014 | Mettler, Jr. | |
| 2006/0287583 A1* | 12/2006 | Mangiardi | ............. A61B 17/02 600/208 |
| 2011/0060192 A1* | 3/2011 | Pastron | ............. A61M 16/0463 600/205 |

(Continued)

FOREIGN PATENT DOCUMENTS

WO   20150164619 A1   11/2015

OTHER PUBLICATIONS

Wang, Tongue-Tied Device, MassGeneral Hospital for Children News, Oct. 30, 2015, 1 page.

*Primary Examiner* — Nicholas Plionis
(74) *Attorney, Agent, or Firm* — Drinker Biddle & Reath LLP

(57) ABSTRACT

A retractor for use in lingual frenotomy has a tapered hollow shield, having a closed distal end and an open proximal rim, a groove opening through the distal end to seat over the lingual frenulum, and a handle extending from the proximal rim in line with the groove.

10 Claims, 4 Drawing Sheets

(56) References Cited

U.S. PATENT DOCUMENTS

| | | | |
|---|---|---|---|
| 2011/0196208 A1* | 8/2011 | Warren | A61B 1/32 600/210 |
| 2011/0213372 A1* | 9/2011 | Keefer | A61B 17/1659 606/85 |
| 2013/0006061 A1* | 1/2013 | Alexander | A61B 1/32 600/235 |
| 2013/0012960 A1* | 1/2013 | Lin | A61B 17/0467 606/138 |
| 2013/0066154 A1* | 3/2013 | Mangiardi | A61B 17/02 600/202 |

* cited by examiner

DEPRESSOR/RETRACTOR

BACKGROUND

Approximately 5% (estimates range from under 4% to nearly 11%) of newborn human children suffer from ankyloglossia, or "tongue-tie," a condition in which the lingual frenulum (a small fold of mucous membrane extending from the floor of the mouth to the midline of the underside of the tongue) is too short, restricting normal movement and function of the tongue. A neonate may be considered to suffer from tongue-tie when the tongue tip is unable to protrude beyond the incisors. However, the degree of restriction, and the severity of the resulting effects, vary from patient to patient. There is no sharp threshold.

Tongue-tie is linked to poor latching/sucking with breastfeeding, which leads to decreases in emptying of the breast as well as in milk transfer. These effects ultimately slow the baby's weight gain. Instead of moving the tongue out of the mouth to "milk" the breast, the neonate is chewing and cupping the nipple tip in an attempt to maintain nipple position. Subsequent damage to the nipple tip may follow with severe pain. The persistence of severe tongue-tie beyond the neonatal period may cause problems with articulation (though usually without speech delay), dental health, social/aesthetic effects (appearance, eating, kissing, playing wind musical instruments, etc.).

The condition can in principle be easily treated by snipping or clipping the restrictive frenulum, an operation known as frenotomy or frenulotomy. Usually, no suture is needed. However, injury to nearby structures (lateral genioglossus muscle and vessels, cheeks, lips, submandibular salivary gland ducts) is to be avoided. Potential adverse outcomes include bleeding, infection, ulceration, pain, cheloid scarring, and recurrence.

It is desirable to use only a topical or local anesthetic, to avoid the complications of more extensive anesthesia. It is therefore necessary to hold the tongue up out of the way with fingers or a depressor, while snipping the frenulum. When treating an alert baby in an outpatient office or doctor's office, it is not always easy to snip the frenulum accurately and cleanly, especially as the baby's small mouth does not allow room for multiple persons to assist, even if additional personnel are available. There is therefore a need for an improved method and apparatus.

SUMMARY OF THE INVENTION

Embodiments of the invention provide a retractor or depressor, and a method of using that retractor, that make it possible more easily to hold the baby's tongue out of the way, protect surrounding tissues from inadvertent damage at least to a considerable extent, and present the frenulum for easy snipping.

According to one embodiment of the invention, there is provided a retractor for use in lingual frenotomy that comprises a tapered hollow shield, having a closed distal end and an open proximal rim, a notch or groove opening through the distal end to seat over the lingual frenulum, and a handle extending from the proximal rim in line with the groove.

The shield may be tapered, so that the distal end is just large enough to allow scissors to be applied to the frenulum, and the proximal end is just small enough to be inserted comfortably into the mouth of a newborn baby. The shield may be wedge-shaped, with the groove extending across the narrow dimension of the wedge.

The groove may be keyhole-shaped, with widened regions at each end.

A base portion of the handle that attaches to the proximal rim of the shield may be approximately aligned with the side of the shield to which it attaches, or angled further away from a centerline of the shield. An outer portion of the handle may be angled further away from the centerline of the shield.

According to an embodiment of the invention, there is provided a method of using the retractor comprising inserting the retractor into the baby's mouth, with the handle at the top (relative to the baby's head), inserting the shield of the retractor under the baby's tongue, seating the notches over the frenulum, and severing the frenulum inside the shield of the retractor.

According to an embodiment of the invention, there is provided a computer program, CAD/CAM file, or other set of computer-readable instructions, which may be stored on a non-volatile tangible computer readable storage medium, operative to cause a suitable computer with a 3-dimensional printer to print out a retractor according to an embodiment of the invention.

BRIEF DESCRIPTION OF THE DRAWINGS

The above and other aspects, features, and advantages of the present invention may be more apparent from the following more particular description of embodiments thereof, presented in conjunction with the following drawings. In the drawings.

DETAILED DESCRIPTION OF THE DRAWINGS

Figure 1:
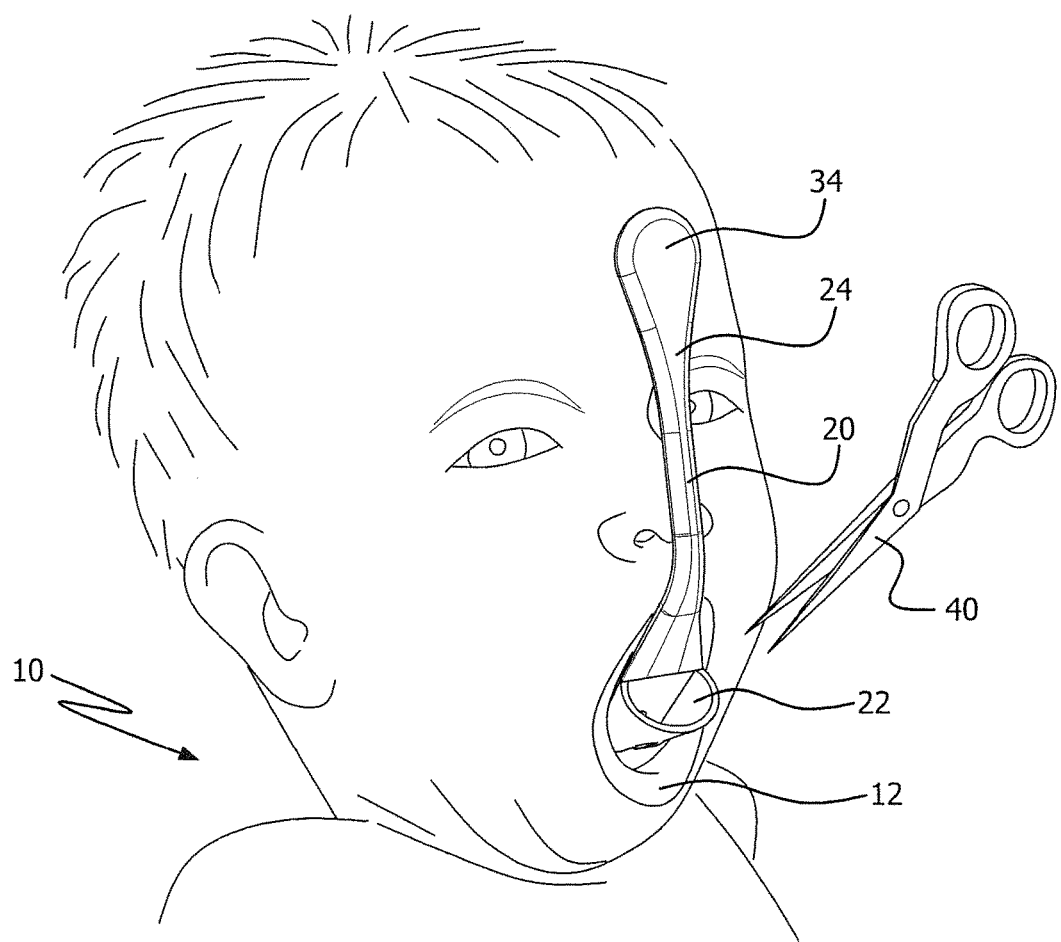
FIG. 1 is a perspective view of a baby's head, with one form of retractor inserted in the mouth.

A better understanding of various features and advantages of the present methods and devices may be obtained by reference to the following detailed description of illustrative embodiments of the invention and accompanying drawings. Although these drawings depict embodiments of the contemplated methods and devices, they should not be construed as foreclosing alternative or equivalent embodiments apparent to those of ordinary skill in the subject art.

Referring to the drawings, a baby indicated generally by the reference numeral 10 has a mouth 12 including a tongue 14. The tongue 14 is restrained by a short lingual frenulum 16.

One form of retractor or depressor indicated generally by the reference numeral 20 comprises a shield 22 and a handle 24. The shield 22 is hollow, and tapers from a proximal rim 26, which is generally D-shaped, to a wedge-shaped distal end 28. The distal end 28 is closed except for a groove 30 across it. The groove 30 ends in widened ends 32, forming a keyhole shape. The handle 24 extends from the straight side of the D-shaped rim 26, and has a base portion 34 that is in line with the adjacent part of the shield 22. Handle base portion 34 and the adjacent part of the shield 22 together forming a flat surface that, as explained below, acts as a tongue depressor. The base portion 34 extends the whole width of the flat side of the D-shaped rim 26. From the base portion 34 of the handle 24, an outer handle portion 36 is angled away from the shield 22.

The retractor 20 may be made from a plastic material that is sufficiently inert or biocompatible to be used in a baby's mouth without significant risk of adverse reaction. The retractor 20 may be made by any convenient method, including molding or printing on a 3-dimensional printer.

In use, the baby's head is typically restrained by an assistant to the operator holding the head in his or her hands. The frenulum is usually anesthetized with a topical or injected local anesthetic.

Figure 2:
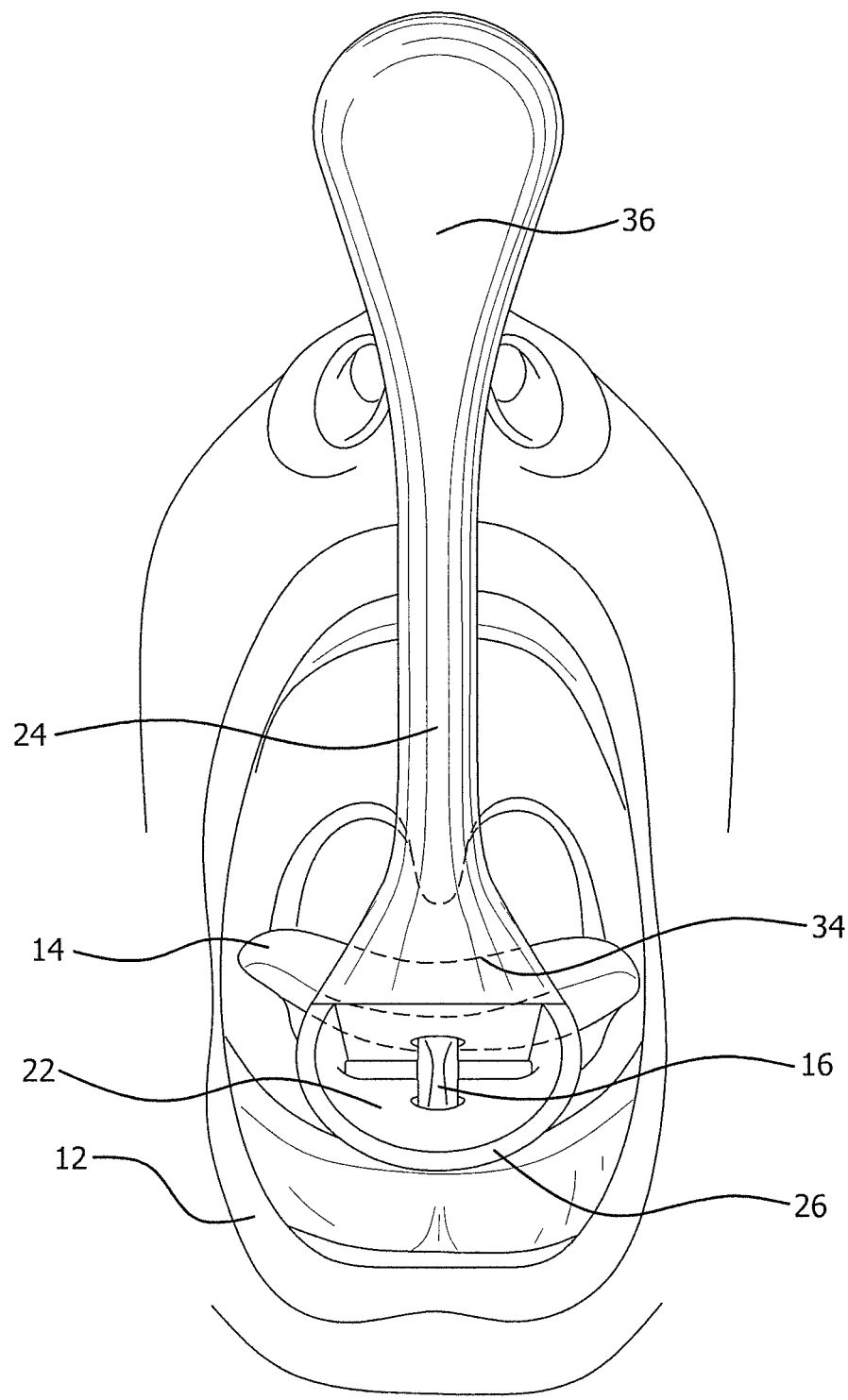
FIG. 2 is a front view of the baby's mouth, with the retractor inserted.
Figure 3:
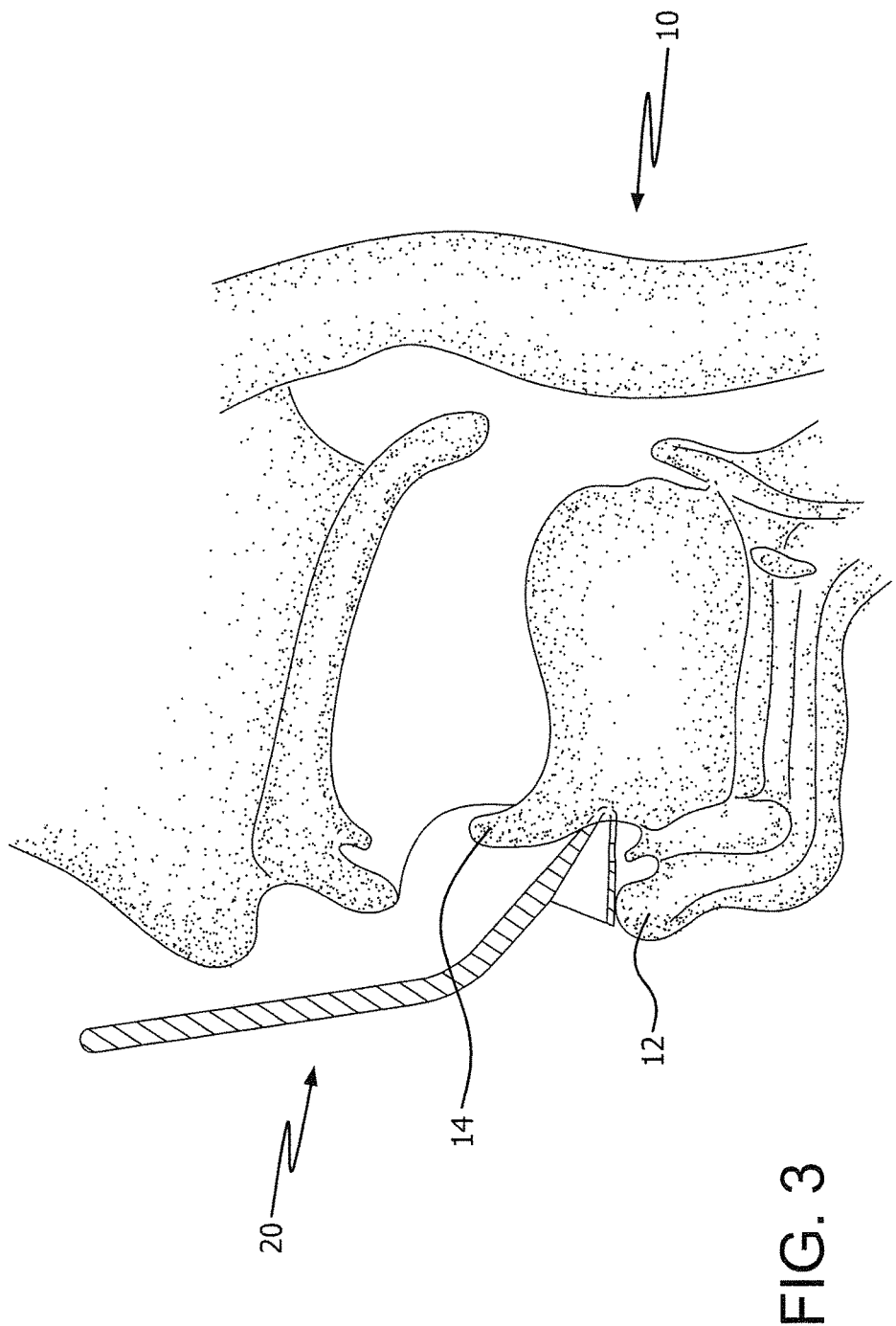
FIG. 3 is a side cross section of the baby's mouth, with the retractor inserted.
Figure 4:
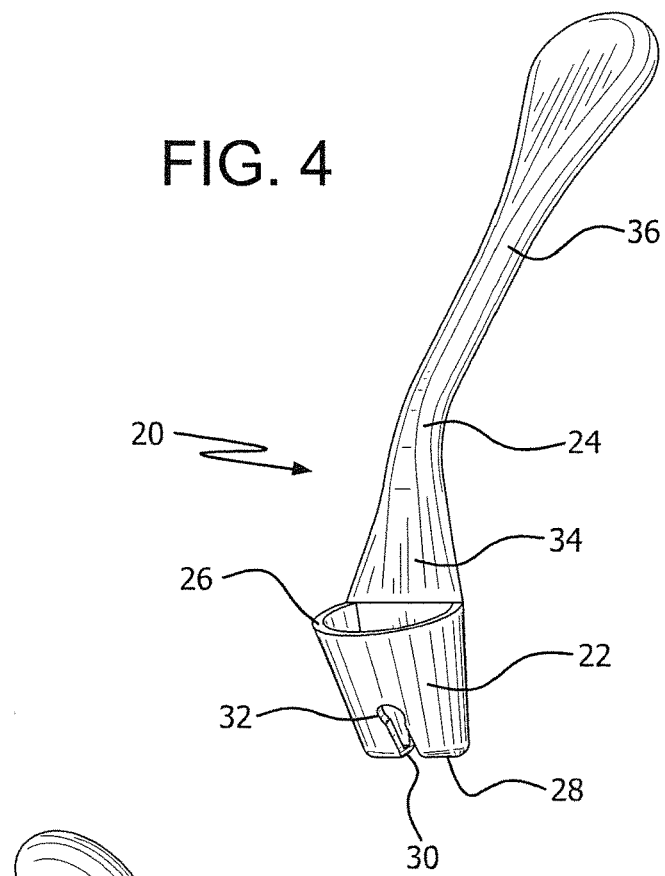
FIG. 4 is a perspective view of the retractor from below.
Figure 5:
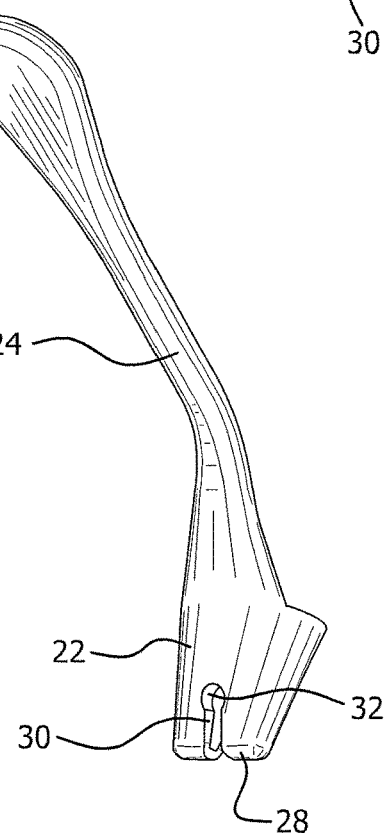
FIG. 5 is a perspective view of the retractor from above.

As shown in FIGS. 1 to 3, the distal end 28 of the retractor 20 can be inserted into the mouth 12 of baby 10, under the tongue 14. The retractor 20 is held with the handle 24 upwards, so that the outer handle portion 36 passes in front of the baby's nose. The groove 30 of retractor 20 is positioned over the frenulum 16 so that the front edge of the frenulum 16 is received in the widened ends 32 of groove 30. The flat side of retractor shield 22 and the base portion 34 of handle 24 serve to hold the baby's tongue 14 up out of the way. The widest part of the retractor shield 22 near the rim 26 prevents the baby's mouth 12 from closing.

A pair of surgical scissors 40 can then be inserted inside the retractor shield 22, to snip the frenulum 16. The shape of shield 12 allows sufficient room to position and operate scissors 40. Because the scissors 40 are inside retractor shield 22, which is closed except for the slot 30, there is comparatively little risk of inadvertently cutting parts of the baby's mouth other than the frenulum 16, even if the baby struggles or moves unexpectedly.

If the procedure is correctly performed, there is little bleeding, but a gauze may be applied with finger pressure for a period from 10 seconds to 3 minutes to prevent significant blood loss. The retractor 20 may remain in place for that period, which may make access to the procedure site easier.

The depressor-retractor 20 has a number of advantages over previously proposed retractors for use in frenotomy. For example:

The closed lateral sides of shield 22 reduce the risk of inadvertent injuries to the venous vessels on the tongue's lateral parts, which are close to the frenulum and/or the lateral muscular lingual tissue. The tongue 14 can move sideways when the baby 10 is crying and/or when the head holding is loose.

The closed underside of shield 22 reduces the risk of cutting or injuring the mouth floor, including the orifices of the submandibular and lingual salivary glands. Mouth floor movements up and down are consistent with a crying newborn baby.

The closed upper side of shield 22 and handle base portion 34 help to incise closer to the posterior wall of the tongue, while preventing injuries to the tongue muscular and venous tissues.

The risk of injury to the operator's fingers from the scissors or from the baby biting, which were possibilities if the operator was using his or her fingers as a retractor, is largely eliminated.

The retractor outward curve or angle of the retractor outer handle portion 36 improves the operator's view of the inherently small operative area in the newborn baby's mouth 12 by situating the hand holding the retractor out of the visual field.

The wide angle opening of retractor shield 22 restricts the tongue's lateral movements as well as the mouth closure movement of the lower jaw.

The parallel grooves 30 in both the upper and lower sides of the retractor shield 22 can better locate and isolate the ligament tie for more precise snipping.

The use of the device reduces the time of the procedure.

As an example of suitable dimensions, the shield 22 may be approximately 0.9 inches (22 mm) long from the rim 26 to the distal end 28, measured along the front or back surface. The front and back may form an included angle of about 40° at the distal end 28, which may be rounded with a radius of about 0.06 inches (1.5 mm). The rim 26 may be approximately 0.9 inches wide. The base portion 34 of the handle 24 may be approximately 1 inch (25 mm) long, with an included angle of about 140° between the base and outer portions of the handle 24.

Those dimensions are believed to provide a retractor 20 that will be suitable for use with most otherwise normal full-term babies, but the size of the shield 22 may be varied by ±15%, or up to ±20%, to provide a better fit for larger or smaller babies.

The handle outer portion 36 may be about 2.5 inches (65 mm) long, 0.25 inches (6 mm) wide along the shaft, and about 0.8 inches (20 mm) wide at the widened end. These dimensions are chosen primarily for comfortable holding by the surgeon or his or her assistant, and individual surgeons may prefer a different shape and/or size.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

For example, although the distal rim of the shield of the retractor is shown in the drawings as D-shaped, with the curved lower side forming approximately two thirds of a circle, other shapes are possible, including a rectangular shape, optionally with more or less rounded corners.

For example, the retractor shown in the drawings was made of ABS plastic, which is sufficiently biocompatible for this purpose. A plastic material lends itself naturally to a shape with fairly thick walls and rounded edges, mitigating any risk of injury caused by the corners or edges of the retractor. However, other materials and shapes are possible.

Accordingly, reference should be made to the appended claims, rather than to the foregoing specification, as indicating the scope of the invention.

The invention claimed is:

1. A retractor for use in lingual frenotomy, comprising:
a tapered hollow shield that has a closed distal end and an open proximal rim, forming a hollow shield with an open interior that widens away from the distal end and is open at the proximal rim;
a groove that extends in a direction across the closed end, opens from the open interior through the distal end to seat over the lingual frenulum, extends proximally into two opposite sides of the shield, and defines a central plane extending proximally; and
a handle that extends from the proximal rim and lies on said plane, wherein a base portion of the handle that attaches to the proximal rim of the shield and an adjacent portion of the shield are flat and in aligned planes to form a surface for raising the tongue of a patient.

2. The retractor of claim 1, wherein the shield is wedge-shaped, having two principal flat faces meeting in an acute angle with the groove extending across the angle between the two principal faces of the wedge.

3. The retractor of claim 1, wherein the groove has a widened region at each end forming a keyhole shape.

4. The retractor of claim 1, wherein an outer portion of the handle is angled away from a side of the handle on which the shield is disposed.

5. The retractor of claim 1, wherein the rim of the shield is D-shaped, with the handle attached at a straight side of the D.

6. The retractor of claim 5, wherein a curved side of the D-shaped rim extends through more than a semicircle and acts as a bite block to keep the mouth open.

7. The retractor of claim 1, which is made of biocompatible material.

8. A method of using a retractor in lingual frenotomy, comprising:
   inserting into a baby's mouth a retractor comprising:
      a tapered hollow shield that has a closed distal end and an open proximal rim, forming a hollow shield with an open interior that widens away from the distal end and is open at the proximal rim, protecting vital tissues in the mouth and caretaker's hands during the frenotomy;
      a groove that extends in a direction across the closed end, opens from the open interior through the distal end to seat over the lingual frenulum, extends proximally into two opposite sides of the shield, and defines a central plane extending proximally; and
      a handle that extends from the proximal rim and lies on said plane, wherein a base portion of the handle that attaches to the proximal rim of the shield and an adjacent portion of the shield are flat and in aligned planes to form a surface for raising the tongue of a patient;
   the retractor being inserted with the handle towards the baby's nose;
   inserting the shield of the retractor under the baby's tongue; and
   seating the groove over the frenulum.

9. The method according to claim 8, further comprising severing the frenulum inside the shield of the retractor.

10. A non-transitory non-volatile tangible computer readable storage medium, comprising:
   computer-readable instructions operative to cause a 3-dimensional printer to print out a retractor for use in lingual frenotomy, the retractor comprising:
      a tapered hollow shield that has a closed distal end and an open proximal rim, forming a hollow shield with an open interior that widens away from the distal end and is open at the proximal rim;
      a groove that extends in a direction across the closed end, opens from the open interior through the distal end to seat over the lingual frenulum, extends proximally into two opposite sides of the shield, and defines a central plane extending proximally; and
      a handle that extends from the proximal rim and lies on said plane, wherein a base portion of the handle that attaches to the proximal rim of the shield and an adjacent portion of the shield are flat and in aligned planes to form a surface for raising the tongue of a patient.

* * * * *